United States Patent
Yoo et al.

(10) Patent No.: US 8,428,683 B2
(45) Date of Patent: Apr. 23, 2013

(54) WEARABLE MONITORING APPARATUS AND DRIVING METHOD THEREOF

(75) Inventors: Hoi-Jun Yoo, Daejeon (KR); Jerald Yoo, Daejeon (KR)

(73) Assignee: Korea Advanced Institute of Science and Technology (KR)

( * ) Notice: Subject to any disclaimer, the term of this patent is extended or adjusted under 35 U.S.C. 154(b) by 510 days.

(21) Appl. No.: 12/702,038

(22) Filed: Feb. 8, 2010

(65) Prior Publication Data

US 2010/0298687 A1    Nov. 25, 2010

(30) Foreign Application Priority Data

May 22, 2009    (KR) .................. 10-2009-0045173

(51) Int. Cl.
*A61B 5/04*    (2006.01)
(52) U.S. Cl.
USPC ........................ 600/391; 600/382; 600/301
(58) Field of Classification Search .................. 600/372, 600/382, 391, 392, 301; 128/898; 439/909
See application file for complete search history.

(56) References Cited

U.S. PATENT DOCUMENTS

| | | | |
|---|---|---|---|
| 5,465,727 A | | 11/1995 | Reinhold, Jr. |
| 5,882,300 A * | | 3/1999 | Malinouskas et al. ........ 600/300 |
| 6,240,316 B1 * | | 5/2001 | Richmond et al. .............. 607/42 |
| 6,416,471 B1 * | | 7/2002 | Kumar et al. ................. 600/300 |
| 6,496,705 B1 * | | 12/2002 | Ng et al. ....................... 455/502 |
| 2003/0100821 A1 * | | 5/2003 | Heller et al. .................. 600/347 |
| 2004/0176805 A1 * | | 9/2004 | Whelan et al. .................... 607/2 |
| 2008/0312520 A1 * | | 12/2008 | Rowlandson et al. ........ 600/372 |

FOREIGN PATENT DOCUMENTS

| | | |
|---|---|---|
| DE | 29620395 | 1/1997 |
| DE | 19607222 | 8/1997 |
| DE | 19749768 | 5/1999 |

* cited by examiner

*Primary Examiner* — Lee S Cohen
*Assistant Examiner* — Erin M Cardinal
(74) *Attorney, Agent, or Firm* — The Belles Group, P.C.

(57) ABSTRACT

Disclosed are a wearable monitoring apparatus and a driving method thereof. The wearable monitoring apparatus comprises: a sensor unit for measuring a biological signal from a human body, wherein the sensor unit is adhered to a skin; and a control unit for searching a location of the sensor unit, supplying power to the sensor unit, and receiving and processing the biological signal from the sensor unit, wherein the control unit is formed to be wearable.

20 Claims, 9 Drawing Sheets

WEARABLE MONITORING APPARATUS AND DRIVING METHOD THEREOF

CROSS-REFERENCE TO RELATED PATENT APPLICATIONS

The present application claims priority under 35 U.S.C. §119 to Korean Patent Application Serial Number 10-2009-0045173, filed May 22, 2009, the entirety of which is hereby incorporated by reference.

BACKGROUND OF THE INVENTION

1. Field of the Invention

The present invention relates to a wearable monitoring apparatus and a driving method thereof.

2. Description of the Related Art

With the development of medical technology, the average lifespan of a human has increased. Meanwhile, the number of persons suffering pain due to a chronic disease has also increased. An important factor of chronic disease is that the faster a disease is discovered and managed, the better chance a person has at recuperation. Accordingly, a medical industry highlights to rapidly search and continuously manage the chronic disease for preventing the condition of the chronic disease from growing worse.

A cardiovascular disease is a representative example of the chronic disease. In order to monitor irregularly occurring arrhythmia, a patient's electrocardiogram (ECG) should be monitored all day and night. To do this, when a conventional Holter monitor is used, a patient should carry a tester in state that an electrode with a plurality of lines is adhered to a body. Owing to this, a conventional monitoring apparatus has various problems. For example, because the patient should carry a wire of plural strands all day, he or she feels a globus syndrome that results in discomfort. Upon using the Holter monitor, because a wet electrode is adhered in most cases, as time goes by, a skin disease can occur in a patient due to stimulation of the skin. This is a problem inconsistent with an original object of a device for continuously sensing a biological signal throughout an individual's daily life in order to monitor a patient's healthy state. In addition to the Holter monitor, a walk blood pressure tester makes a patient feel a globus syndrome.

In order to solve such problems, various technologies have been developed. A health management system known as "Toumaz Technology" is one such example of the technology. The health management system includes a wireless adhesive plaster type ECG patch and a monitoring data collecting unit for collecting data in a terminal such as a portable phone. A main disadvantage of the health management system is that the wireless adhesive plaster type ECG patch needs a separate power supply (battery or the like). In this case, since a patient must continue to live and carry on his daily routine with the battery adhered to the skin, when the patient sweats during a continuous monitoring procedure, a chemical reaction occurs which may potentially cause a safety problem.

Moreover, the wireless adhesive plaster type ECG patch and the monitoring data collecting unit communicate with each other based on a wireless communication using a radio frequency. Such a wireless communication can induce physiological interference and infringement danger. However, because security and reliance are of utmost importance in characteristics of a device having to monitor a biological signal, a conventional approach using wireless communication is significantly dangerous.

SUMMARY OF THE INVENTION

The present invention has been made in view of the above problems, and it is an object of the present invention to provide a wearable monitoring apparatus that may efficiently and safely monitor a biological signal without the wearers having to suffer from globus syndrome during their daily lives.

It is another object of the present invention to provide a driving method of a wearable monitoring apparatus.

In accordance with an exemplary embodiment of the present invention, there is provided a wearable monitoring apparatus for continuously monitoring a biological signal comprising: a sensor unit for measuring a biological signal from a human body, wherein the sensor unit is adhered to a skin; and a control unit for searching a location of the sensor unit, supplying power to the sensor unit, and receiving and processing the biological signal from the sensor unit, wherein the control unit is formed to be wearable.

In a preferred embodiment, the sensor unit may comprise: an adhesive layer having adhesion and flexibility; an inductor for connecting to the control unit by wireless means using near field coupling; a sensing electrode for sensing the biological signal; a sensor chip for transmitting a response signal containing type information of the sensor unit to the control unit in response to a searching signal from the control unit, measuring the biological signal using the sensing electrode, and transmitting the measured biological signal to the control unit; and a molding portion formed to cover the sensor chip to prevent the sensor chip from being damaged from an outside, wherein at least one of the inductor and the sensing electrode is formed by printing a conductive material on a fiber.

In another preferred embodiment, the control unit may comprise: a plurality of inductors for connecting to the sensor unit by wireless means using near field coupling, wherein the plurality of inductors are arrayed in a coordinate matrix pattern; a power supply for providing the searching signal and power to be transmitted to the sensor unit; and a network controller for transmitting the searching signal in a set coordinate order using the plurality of inductors, receiving the response signal, storing the type information of the sensor unit and coordinate information of an inductor having received the response signal, supplying power to the sensor unit to meet set sensing cycle and power transmission strength according to a type of the sensor unit using the inductor having received the response signal, receiving the biological signal measured by the sensor unit, and storing the received biological signal, wherein the network controller is connected to the plurality of inductors, wherein the plurality of inductors are formed by printing a conductive material on a fiber.

In may be preferred that the sensory unit comprise: an adhesive layer having adhesion and flexibility; a first connector for connecting to the control unit by wired means, wherein a first connector is attached and detached to the control unit; a sensing electrode for sensing the biological signal; a sensor chip for transmitting a response signal containing type information of the sensor unit to the control unit in response to a searching signal from the control unit, measuring the biological signal using the sensing electrode, and transmitting the measured biological signal to the control unit; and a molding portion formed to cover the sensor chip to prevent the sensor chip from being damaged from an outside, wherein the sensing electrode is formed by printing a conductive material on a fiber.

In a further preferred embodiment, the control unit can comprise: a plurality of second connectors for connecting to the sensor unit by wired means using the first connector, wherein the plurality of second connectors are arrayed in a coordinate matrix pattern, attached and detached to the sensor unit; a power supply for providing the searching signal and power to be transmitted to the sensor unit; and a network controller for transmitting the searching signal in a set coordinate order using the plurality of second connectors, receiving the response signal, storing the type information of the sensor unit and coordinate information of a second connector having received the response signal, transferring power to the sensor unit to meet a set sensing cycle and power transmission strength according to a type of the sensor unit using the second connector having received the response signal, receiving the biological signal measured by the sensor unit, and storing the received biological signal, wherein the network controller is connected to the plurality of second connectors.

In a preferred embodiment, the first connector and the second connector can be configured in a form of a Velcro, a button, zipper, or a conductive contact, and can be made of a conductive material.

In accordance with another embodiment of the present invention, there is provided a sensor unit of a wearable monitoring apparatus adhered to a human body and measuring a biological signal comprising: an adhesive layer having adhesion and flexibility; an inductor for connecting to a control unit by wireless means using near field coupling, the control unit collecting the biological signal measured by the sensor unit; a sensing electrode for sensing the biological signal; a sensor chip for transmitting a response signal to the control unit in response to a searching signal from the control unit, receiving power from the control unit to measure the biological signal using the sensing electrode, and transmitting the measured biological signal; and a molding portion formed to cover the sensor chip to prevent the sensor chip from being damaged from an outside, wherein at least one of the inductor and the sensing electrode is formed by printing a conductive material on a fiber.

In accordance with yet another embodiment of the present invention, there is provided a sensor unit of a wearable monitoring apparatus adhered to a human body and measuring a biological signal comprising: an adhesive layer having adhesion and flexibility; a connector for connecting to a control unit by wired means, the control unit collecting the biological signal measured by the sensor unit, wherein the connector is attached and detached to the control unit; a sensing electrode for sensing the biological signal; a sensor chip for transmitting a response signal containing type information of the sensor unit to the control unit in response to a searching signal from the control unit, measuring the biological signal using the sensing electrode, and transmitting the measured biological signal to the control unit; and a molding portion formed to cover the sensor chip to prevent the sensor chip from being damaged from an outside, wherein the sensing electrode is formed by printing a conductive material on a fiber.

In accordance with a still further embodiment of the present invention, there is provided a control unit of a wearable monitoring apparatus collecting a biological signal measured by a sensor unit adhered to a human body comprising: a plurality of inductors for connecting to the sensor unit by wireless means using near field coupling, wherein the plurality of inductors are arrayed in a coordinate matrix pattern; a power supply for providing a searching signal and power to be transmitted to the sensor unit; and a network controller for transmitting the searching signal in a set coordinate order using the plurality of inductors, receiving a response signal containing type information of the sensor unit as a response to the searching signal, storing the type information of the sensor unit and coordinate information of an inductor having received the response signal, transferring power to the sensor unit to meet a set sensing cycle and power transmission strength according to a type of the sensor unit using the inductor having received the response signal, receiving the biological signal measured by the sensor unit, and storing the received biological signal, wherein the network controller is connected to the plurality of inductors, wherein the plurality of inductors are formed by printing a conductive material on a fiber.

In another exemplary embodiment, there is provided a control unit of a wearable monitoring apparatus collecting a biological signal measured by a sensor unit adhered to a human body comprising: a plurality of connectors for connecting to the sensor unit by wired means, wherein the plurality of connectors are arrayed in a coordinate matrix pattern, attached and detached to the sensor unit measuring the biological signal; a power supply providing a searching signal and power to be transmitted to the sensor unit; and a network controller for transmitting the searching signal in a set coordinate order using the plurality of connectors, receiving a response signal containing type information of the sensor unit as a response to the searching signal, storing the type information of the sensor unit and coordinate information of a connector having received the response signal, supplying power to the sensor unit to meet a set sensing cycle and power transmission strength according to a type of the sensor unit through the connector having received the response signal, receiving the biological signal measured by the sensor unit, and storing the received biological signal, wherein the network controller is connected to the plurality of connectors.

In one embodiment, the method of driving the wearable monitoring apparatus may comprise the steps of: (i) automatically searching a location of the sensor unit; (ii) supplying power to the sensor unit and measuring a biological signal; and (iii) transmitting the biological signal measured by the sensor unit to the control unit.

It may be preferred that step (i) further comprise: transmitting a searching signal in a set coordinate order using a plurality of inductors arrayed on the control unit in a coordinate matrix pattern; checking whether a response signal containing type information of the sensor unit as a response to the searching signal; and storing the response signal and coordinate values of an inductor having received the response signal when the response signal is received, and In a preferred embodiment, step (ii) can further comprise: recognizing a type of the sensor unit using the response signal; supplying power with a set sensing cycle and power transmission strength to the sensor unit using an inductor having received the response signal according to the recognized type of the sensor unit; and measuring the biological signal using the sensor unit, wherein the sensor unit and the control unit transmit and receive data in a wireless connection manner using near field coupling to and from each other.

Ina preferred embodiment, step (i) may comprise transmitting the searching signal using an inductor on next coordinates after storage of the response signal and the coordinate values of an inductor having received the response signal is terminated, and checks whether the response signal is received.

In another preferred embodiment, step (i) may comprise: transmitting a searching signal in a set coordinate order using a plurality of connectors arrayed on the control unit in a coordinate matrix pattern; checking whether a response signal containing type information of the sensor unit as a response to the searching signal; and storing the response signal and coordinate values of an connector having received the response signal when the response signal is received, and In yet another preferred embodiment, step (ii) can comprise: recognizing a type of the sensor unit using the response signal; supplying power with a set sensing cycle and power transmission strength to the sensor unit using a connector having received the response signal according to the recognized type of the sensor unit; and measuring the biological signal using the sensor unit, wherein the sensor unit and the control unit transmit and receive data in a wired connection manner using the connector to and from each other.

In a still further preferred embodiment, step (i) may include transmitting the searching signal using a connector on next coordinates after storage of the response signal and the coordinate values of a connector having received the response signal is terminated, and checks whether the response signal is received.

In an even further preferred embodiment, step (ii) can include supplying power with different sensing cycles to respective sensor units when there are at least two types of the sensor units.

In one preferred embodiment, step (iii) can comprise: amplifying, filtering and converting into digital data the biological signal measured by the sensor, and transmitting the digital data to the control unit; and compressing, encrypting, and storing the digital biological signal transmitted to the control unit.

In the present invention, because a dry electrode is used so as not to stimulate the skin at the point of adhesion for an excess amount of time, convenience can be increased.

Moreover, since a control unit is manufactured in the form of an abdominal bandage or article of clothing, a sensor unit does not need a separate power supply. Accordingly, it is not necessary to install a battery in the vicinity of the skin. Consequently, upon adhering the sensor unit, a wearable monitoring apparatus can be stably used despite the potential for the sensor unit to come into contact with sweat or water.

When the conventional wireless communication using a radio frequency is utilized, physiological interference and infringement danger can occur. In contrast, in accordance with the present invention, since a distance between a sensor unit adhered to a body and a control unit overlapped on the sensor unit in a form of an abdominal bandage or clothes is very short, near field coupling can be used. This is robust to interference and security and increases the reliance of communication.

BRIEF DESCRIPTION OF THE DRAWINGS

The objects, features and advantages of the present invention will be more apparent from the following detailed description in conjunction with the accompanying drawings, in which.

DETAILED DESCRIPTION OF EXEMPLARY EMBODIMENTS

[Wearable Monitoring Apparatus]

Figure 1:
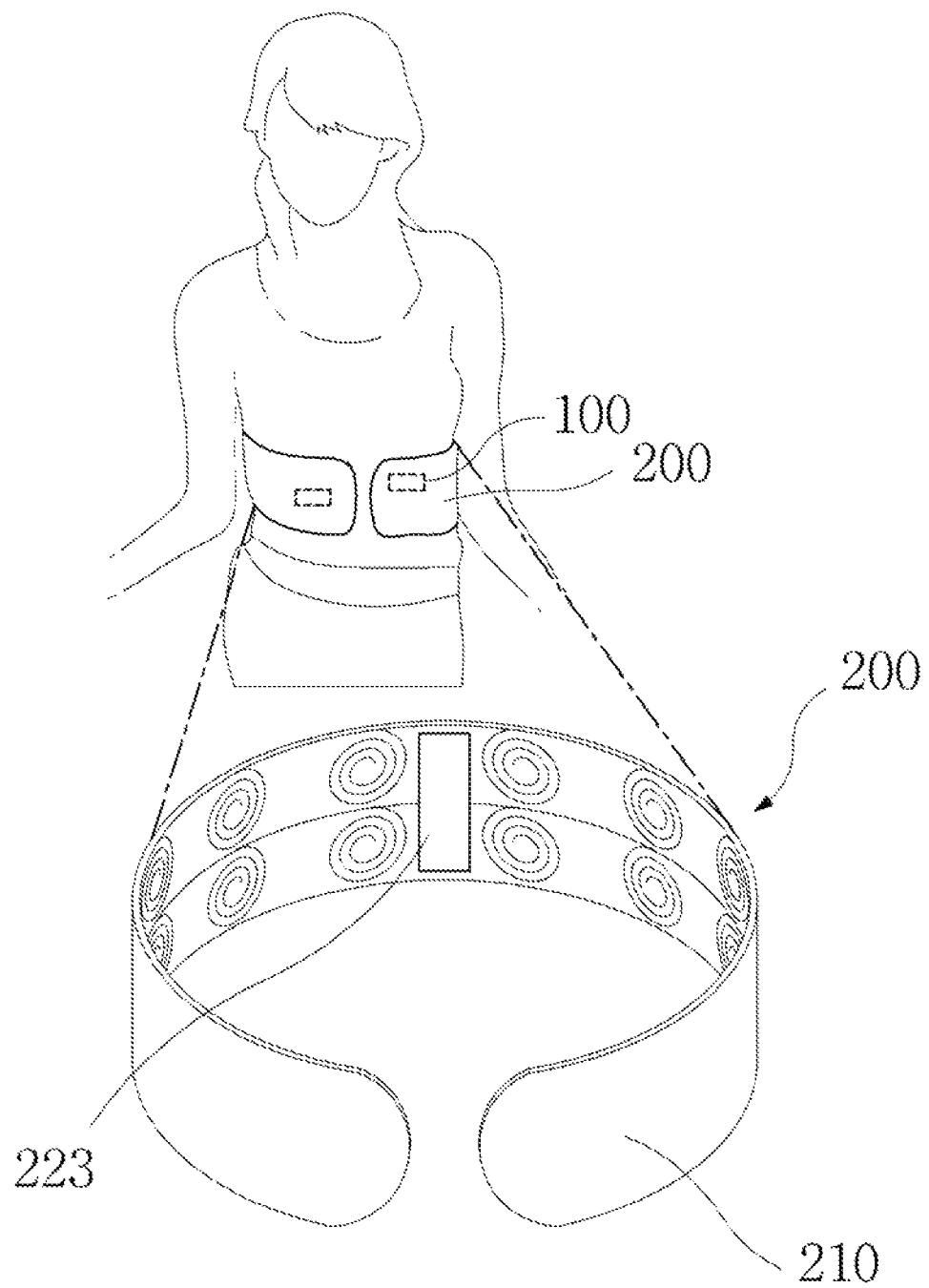
FIG. 1 is a view illustrating a configuration of a wearable monitoring apparatus in accordance with an embodiment of the present invention.

Hereinafter, a wearable monitoring apparatus in accordance with a preferred embodiment of the present invention will be described in detail referring to the accompanying drawings. The same reference numerals are used throughout the drawings to refer to the same or like parts. Detailed descriptions of well-known functions and structures incorporated herein may be omitted to avoid obscuring the subject matter of the present invention.

[First Embodiment]

FIG. 1 is a view illustrating a configuration of a wearable monitoring apparatus in accordance with an embodiment of the present invention.

Referring to FIG. 1, the wearable monitoring apparatus in accordance with an embodiment of the present invention includes a sensor unit 100 and a control unit 200.

Figure 2:
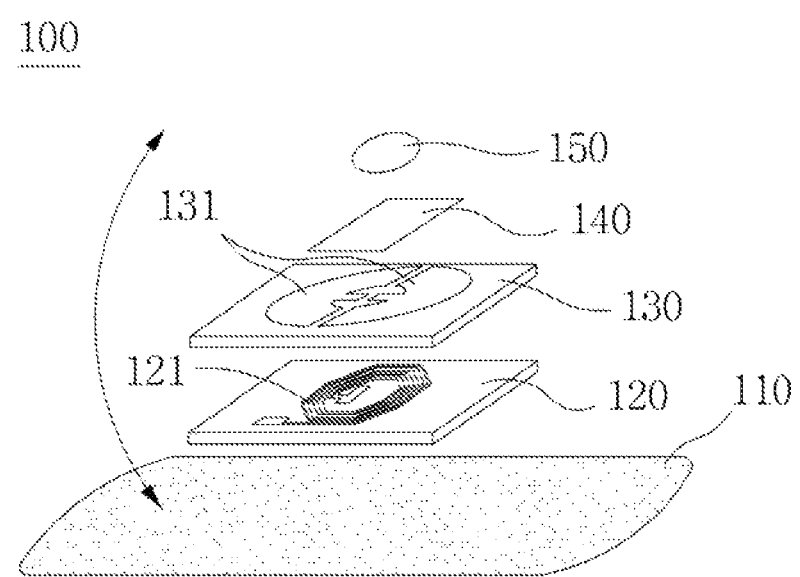
FIG. 2 is a view illustrating a configuration of a sensor unit of a wearable monitoring apparatus in accordance with a first embodiment of the present invention.

FIG. 2 is a view illustrating a configuration of a sensor unit 100 of a wearable monitoring apparatus in accordance with a first embodiment of the present invention.

Referring to FIG. 2, the sensor unit 100 is attached or detached to or from a skin, and is configured to measure a biological signal from a human body. The sensor unit 100 may be a sensor for measuring electrocardiogram (ECG), glycemic index (GI), blood pressure or pulse, and the sensor unit 100 measures a biological signal in the same manner as in a conventional sensor for measuring a biological signal.

The sensor unit 100 includes an adhesive layer 110, an inductor (or antenna) 121 for data communication, a sensing electrode 131, a sensor chip 140, and a molding portion 150.

The adhesive layer 110 may be made in a form of an adhesive plaster with adhesion and flexibility.

The inductor 121 is an antenna for wireless communication, and is configured to be connected to inductors of the control unit 200 by wireless means using near field coupling such as inductive coupling. The inductor 121 may be formed by printing a conductive material such as a silver paste to be wound in a snail form on a fiber 120 using screen printing or sputtering. The inductor 121 may be disposed on the adhesive layer 110.

The sensing electrode 131 may sense a biological signal from the human body. The sensing electrode 131 may be a conductive material such as a silver paste printed on the fiber 130 by screen printing or sputtering.

The sensor chip 140 transmits a response signal containing information regarding a type of the sensor unit 100 to the control unit 200 in response to a searching signal from the control unit 200. The searching signal is a signal having a predetermined power level transmitted by the control unit 200 in order to recognize a location and a type of the sensor unit 100. Upon reception of the searching signal, the sensor chip 140 transmits the response signal to the control unit 200. After transmitting the response signal to the control unit 200, the sensor chip 140 receives power from the control unit 200 using the inductor 121 and measures a biological signal using the sensing electrode 131. The sensor chip 140 may amplify, filter, and convert the measured biological signal into digital data, and transmit the digital data, or may transmit the measured biological signal in a raw data state.

When the sensor unit 100 is adhered to a skin, the molding portion 150 can be configured to cover only the sensor chip 140 so as to minimize a globus syndrome. Meanwhile, the molding portion 150 can be configured to cover all of the inductor 121, the sensing electrode 131, and the sensor chip 140 if necessary.

A formation order of the inductor 121, the sensing electrode 131, and the sensor chip 140 in the sensor unit 100 may be changed, and one or plural layers can be formed therein.

Figure 3:
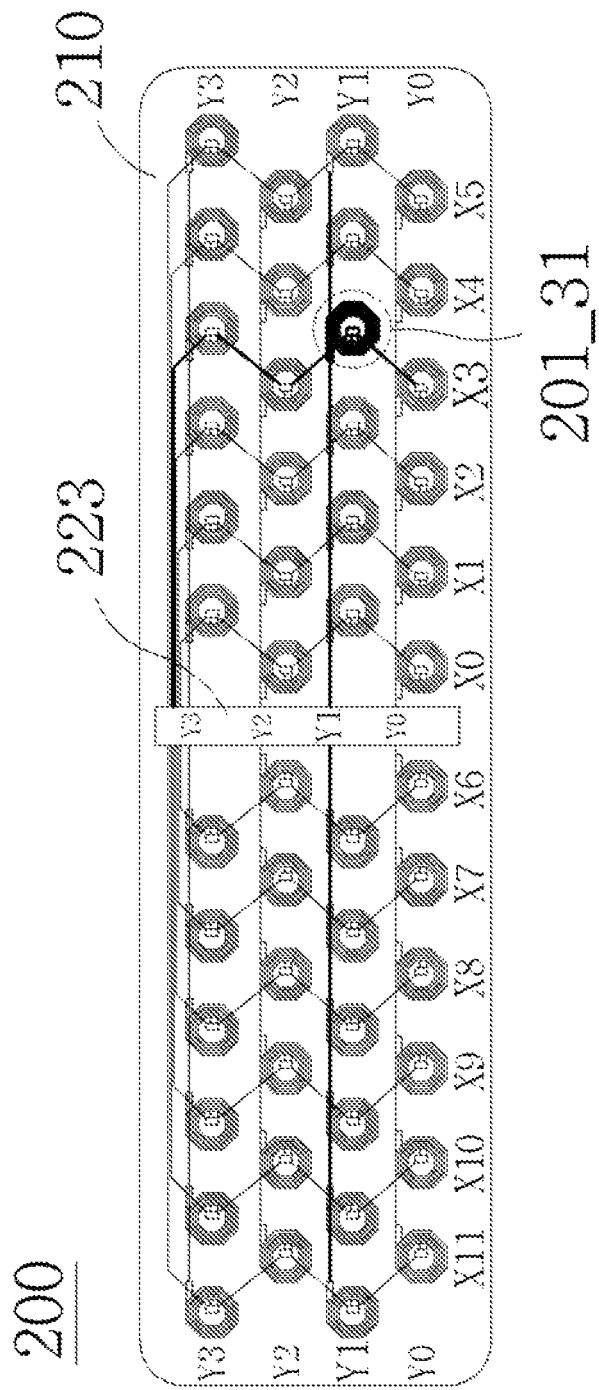
FIG. 3 is a view illustrating a configuration of a control unit of a wearable monitoring apparatus in accordance with a first embodiment of the present invention.

FIG. 3 is a view illustrating a configuration of a control unit 200 of a wearable monitoring apparatus in accordance with a first embodiment of the present invention.

Referring to FIG. 3, the control unit 200 may include an abdominal bandage 210, a plurality of 12×4 orthogonally arrayed inductors, a network controller 223 connected to the plurality of inductors, and a power supply (not shown) providing a searching signal to be transmitted and power to the sensor unit 100. An article of clothing can be substituted for the abdominal bandage 210.

The control unit 200 periodically or non-periodically recognizes a location and a type of the sensor unit 100 using a type of near field coupling such as an inductive coupling communication system. Further, the control unit 200 supplies power with a set sensing cycle and a power transmission strength to the sensor unit 100 according to the recognized type of the sensor unit 100. Moreover, the control unit 200 receives and processes the biological signal measured by the sensor unit 100 to allow a continuous health monitoring in everyday life.

As shown in FIG. 3, the plurality of inductors are arrayed on the abdominal bandage 210 in a coordinate matrix pattern (Xn, Yn). Furthermore, the plurality of inductors may be configured to be connected to the inductor 121 of the sensor unit 100 by wireless means using near field coupling such as inductive coupling. Although the plurality of inductors are orthogonally arrayed in the embodiment, the present invention is not limited thereto. For example, the plurality of inductors may be cross arranged or concentrated on a specific part of an article of clothing (underwear) or the abdominal bandage 210. The plurality of inductors may be formed by printing a conductive material such as a silver paste to be wound in a snail form on the fiber 120 using screen printing or sputtering.

Figure 4:
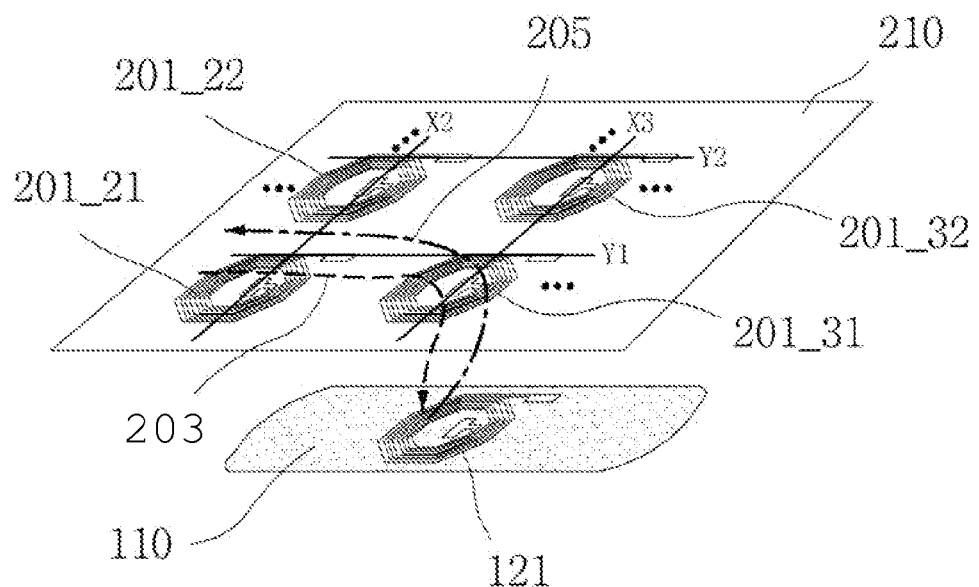
FIG. 4 is a view illustrating selecting and operating methods of a sensor unit of the wearable monitoring apparatus in accordance with a first embodiment of the present invention.

The network controller 223 automatically searches for the location and the type of the sensor unit 100 that is adhered to a predetermined part of a human body. To do this, the network controller 223 transmits a searching signal in a coordinate order determined by the plurality of inductors. Upon reception of the searching signal, the sensor unit 100 receives a response signal containing information about the type of the sensor unit 100 as a response to the searching signals. The searching signal can be sequentially transmitted in a set coordinate order using the plurality of inductors. For example, while the searching signal is being transmitted using an inductor among the plurality of inductors disposed on predetermined coordinates, if the network controller 223 does not receive a response signal from the sensor unit 100 for a predetermined time, the network controller 223 records completion of a valid time capable of transmitting the searching signal to an inductor on the coordinates, and moves its location to an inductor of next coordinates to transmit the searching signals. In this way, as shown in FIG. 4, when the sensor unit 100 is present at a position corresponding to (X3, Y1) coordinates during searching, the network controller 223 receives a response signal from the sensor unit 100 as a response to the searching signal 203. At this time, the network controller 223 stores information relating to the type of the sensor unit 100 included in the response signal 205 and coordinate information (X3, Y1) of an inductor 201_31 having received the response signal 205 when the response signal 205 is received. Upon searching all positions, the network controller 223 terminates automatic sensor searching.

After termination of the automatic sensor searching, the network controller 223 controls an operation of the sensor unit 100 based on the type information of the sensor unit 100 and coordinate information of an inductor having received the response signal 205. Prior to controlling the operation of the sensor unit 100, the network controller 223 checks what type (for example, a sensor for measuring electrocardiogram (ECG), glycemic index (GI), blood pressure, or pulse) is the searched sensor unit 100. In this case, since required operation cycles and power amounts differ according to sensors, the network controller 223 previously determines a set sensing cycle and power transmission strength according to a type of the sensor unit 100, and then supplies power to meet them. In this case, the network controller 223 supplies power from the control unit 200 to the sensor unit 100 using an inductor 201_31 on stored (X3, Y1) coordinates and the inductor 121 of the sensor unit 100. At this time, power is produced by inductive coupling to make a power source to be used in a circuit itself, the sensor unit 100 may perform an operation measuring a biological signal without a separate power source.

In the meantime, upon reception of a biological signal in a raw data state from the sensor unit 100, the network controller 223 may amplify, filter, and convert the received biological signal into digital data, and store it using compression/encryption.

[Second Embodiment]

There is a difference in a communication system between a sensor unit and a control unit upon comparing the second embodiment of the present invention with the first embodiment. The first embodiment of the present invention uses a wireless communication system, whereas the second embodiment of the present invention uses a wired communication system.

A construction of the second embodiment of the present invention is similar to that of the first embodiment, except for a first connector 320 and a second connector 401 configured to directly connect the sensor unit 300 and the control unit 400 for wired communication. Hereinafter, a construction of the second embodiment associated with differences from the first embodiment will be described.

Figure 5:
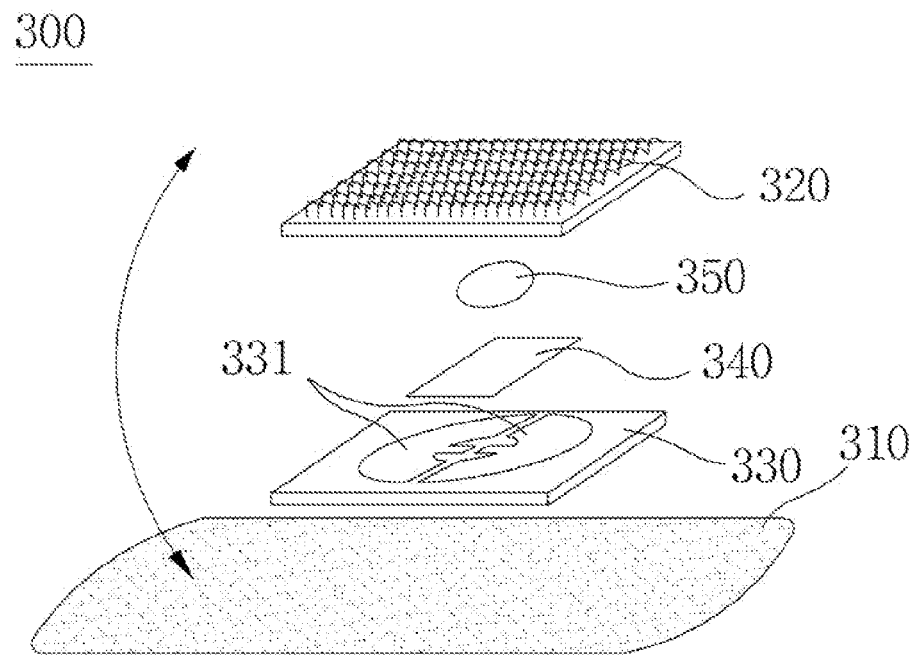
FIG. 5 is a view illustrating a sensor unit in accordance with a second embodiment of the present invention.

FIG. 5 is a view illustrating a sensor unit 300 in accordance with a second embodiment of the present invention.

Referring to FIG. 5, the sensor unit 300 includes an adhesive layer 310, a first connector 320, a sensing electrode 331, a sensor chip 340, and a molding portion 350. The sensing electrode 331 may he a conductive material such as a silver paste printed on a fiber 330 by screen printing or sputtering.

Constructions of the adhesive layer 310, the sensing electrode 331, the sensor chip 340, and the molding portion 350 of the sensor unit 300 in accordance with a second embodiment of the present invention are identical with those of the adhesive layer 110, the sensing electrode 131, the sensor chip 140, and the molding portion 150 of the sensor unit 100 in accordance with the first embodiment. However, the first connector 320 of the sensor unit 300 in accordance with a second embodiment of the present invention differs from the inductor 121 of the sensor unit 100 in accordance with the first embodiment, respectively. The first connector 320 can be attached and detached to and from the control unit 400. Upon being attached, the first connector 320 is configured to be connected to the control unit 400 by wired means.

Figure 6:
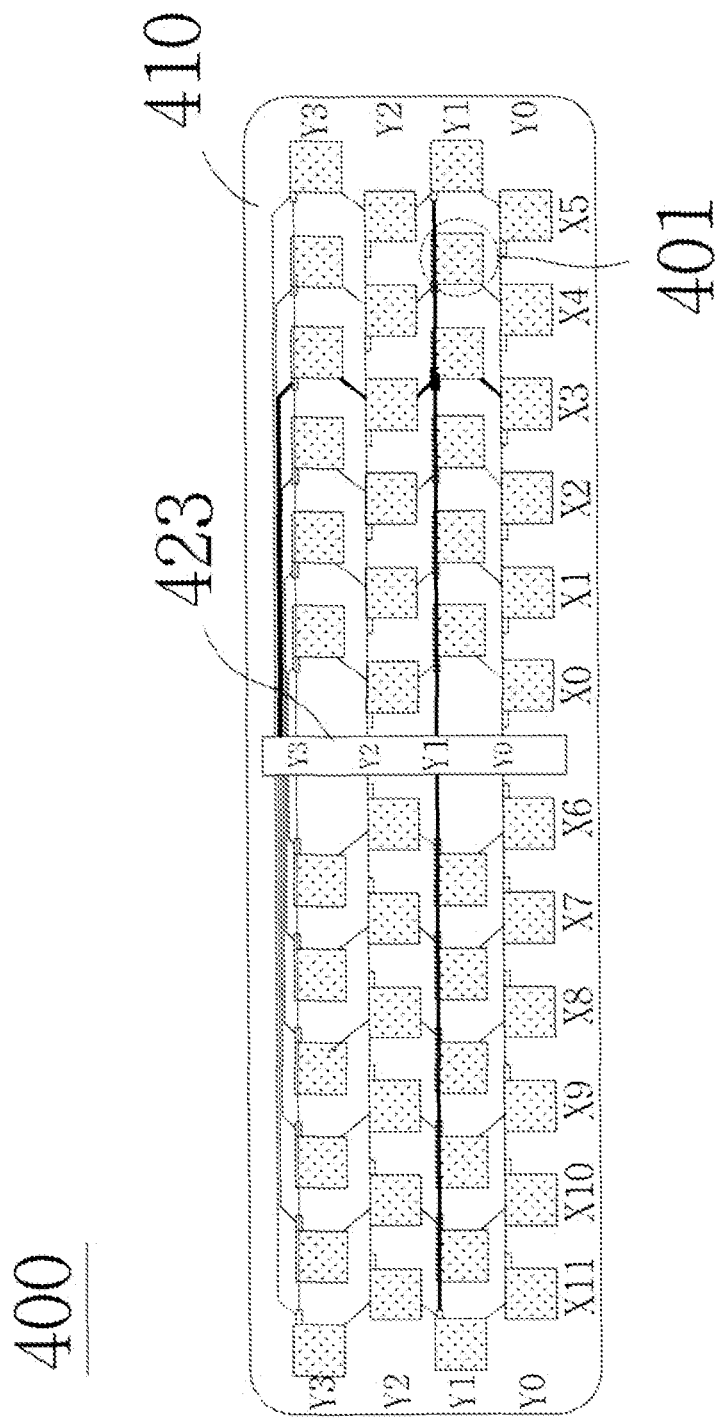
FIG. 6 is a view illustrating a control unit in accordance with a second embodiment of the present invention.

FIG. 6 is a view illustrating a control unit 400 in accordance with a second embodiment of the present invention.

Referring to FIG. 6, the control unit 400 in accordance with a second embodiment of the present invention includes an abdominal bandage 410, a plurality of second connectors 401, a network controller 423, and a power supply (not shown).

The abdominal bandage 410, the network controller 423, and the power supply of the control unit 400 in accordance with a second embodiment of the present invention have the same constructions as those of the abdominal bandage 210, the network controller 223, and the power supply of the control unit 200 in accordance with the first embodiment. However, the second connector 401 of the control unit 400 in accordance with a second embodiment of the present invention differs from the inductor 201 of the control unit 200 in accordance with the first embodiment. As shown in FIG. 6, the second connector 401 is disposed in a coordinate matrix pattern. The second connector 401 can be attached and detached to and from the sensor unit 300. Upon being attached, the second connector 401 is configured to be connected to the sensor unit 300 by wired means.

As described above, the sensor unit 300 and the control unit 400 can communicate with each other by a wired connection method due to a direct contact of the first connector 320 and the second connector 401.

The first connector 320 and the second connector 401 may be configured in a form of a Velcro, a zipper, a button, or a conductive contact to attach and detach the sensor unit 300 and the control unit 400 to and from each other. Further, the first connector 320 and the second connector 401 enable the sensor unit 300 and the control unit to exchange an electric signal with each other.

Figure 7:
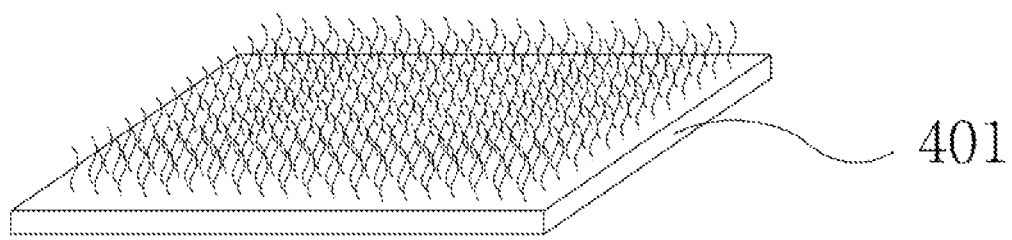
FIG. 7 is a view illustrating a configuration of a second connector included in the control unit of the second example shown in FIG. 6.

When the first connector 320 and the second connector 401 is configured in the form of a Velcro, the first connector 320 is constructed to have a rough surface as shown in FIG. 5, and the second connector 401 is constructed to have a smooth surface as shown in FIG. 7, thereby minimizing a globus syndrome upon wearing the control unit 400. When the first connector 320 and the second connector 401 are configured in the form of a button, they can be implemented by a snap fastener or a button using a magnet. Moreover, the first connector 320 and the second connector 401 are configured in a form of a conductive contact, they can be implemented by a pair of plane magnets. In addition, the first connector 320 and the second connector 401 can be configured by a conductive contact of a clip or puzzle form.

[Driving Method of Wearable Monitoring Apparatus]

Hereinafter, a driving method of a wearable monitoring apparatus in accordance with the present invention will be described with reference to the accompanying drawings. As mentioned previously, the first embodiment and the second embodiment are almost identical with each other except for using wired and wireless communication systems. Accordingly, a driving method of a wearable monitoring apparatus in accordance with a first embodiment will be described in detail as a representative example of a driving method of a wearable monitoring apparatus.

Figure 8:
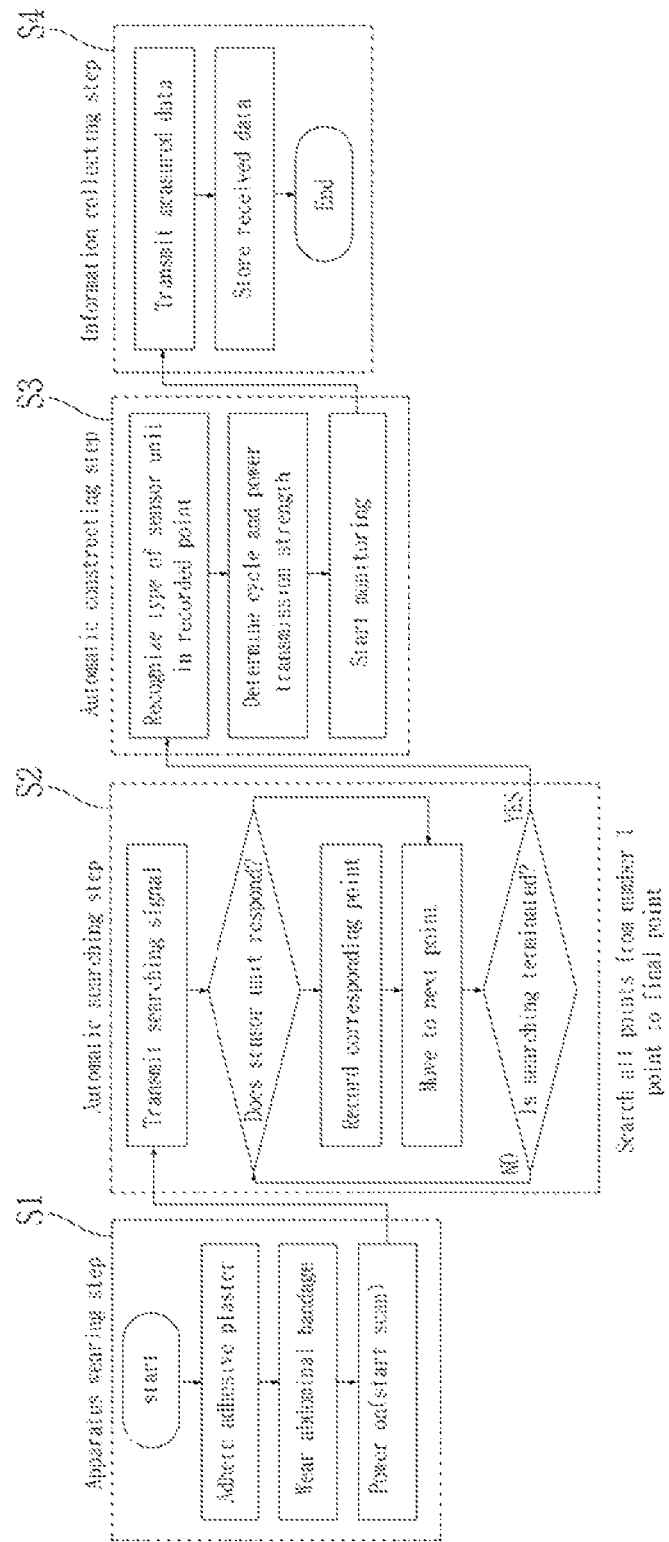
FIG. 8 is a flow chart illustrating a driving method of a wearable monitoring apparatus in accordance with an embodiment of the present invention.

FIG. 8 is a flow chart illustrating a driving method of a wearable monitoring apparatus in accordance with an embodiment of the present invention.

Referring to FIG. 8, a driving method of a wearable monitoring apparatus in accordance with a first embodiment of the present invention includes an apparatus wearing step (S1), an automatic searching step (S2), an automatic constructing step (S3), and an information collecting step (S4).

In the apparatus wearing step (S1), after a sensor unit 100 is adhered to a monitoring part and a user wears a control unit 200, a user turns-on power and starts searching.

In the automatic searching step (S2), a location of the sensor unit 100 is found, and a type of the sensor unit 100 is recognized. To do this, a searching signal is transmitted in a set coordinate order by a plurality of inductors disposed in the control unit 200. When the searching signal is transmitted using an inductor on first coordinates, it is checked whether the sensor unit 100 responds to the transmitted searching signal. If there are no responses after a predetermined time elapses, termination of a search valid time in a currently searched point is recorded and the searching signal is transmitted to an inductor of the next coordinates. When a response signal is received using an inductor of certain coordinates, after the received response signal and coordinate information of an inductor having received the response signal are stored, the searching signal is transmitted to an inductor of the next coordinates. In the foregoing manner, when all points are searched, the automatic searching step (S2) is terminated.

Figure 9:
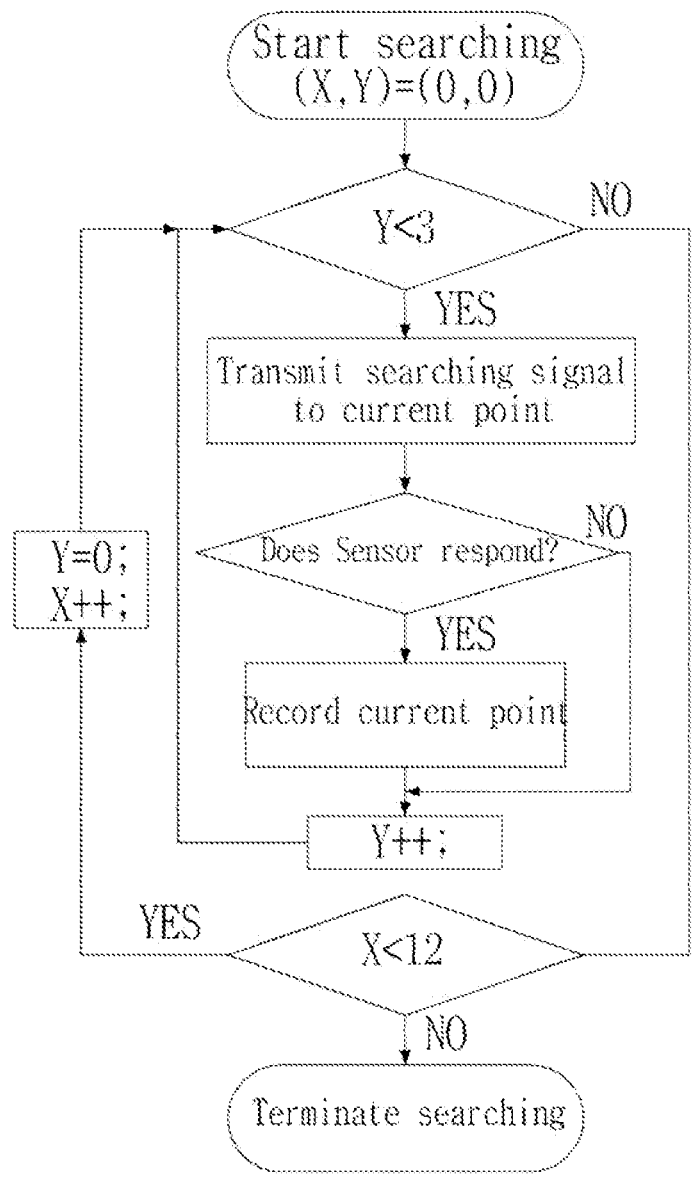
FIG. 9 and FIG. 10 are views illustrating an automatic searching method of a control unit in accordance with an embodiment of the present invention.
Figure 10:
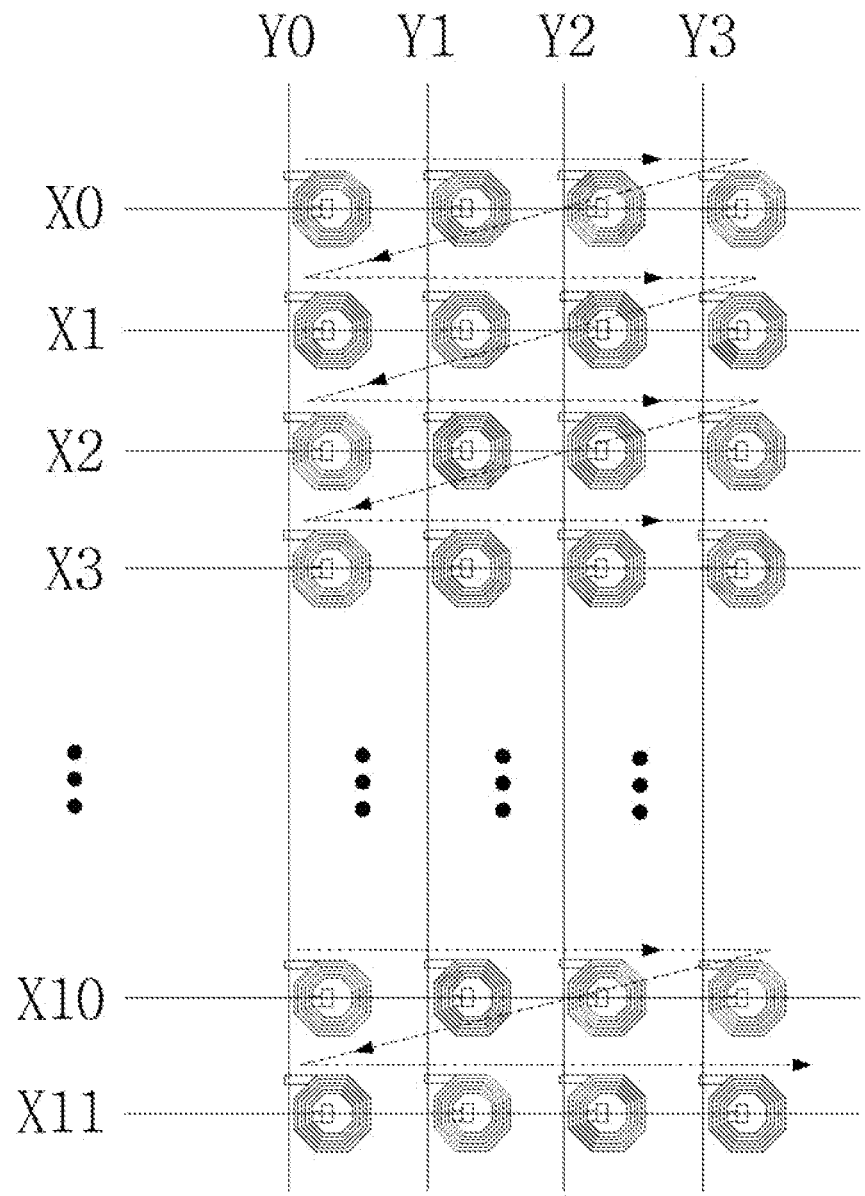

FIG. 9 and FIG. 10 are views illustrating the automatic searching step (S2) using the control unit 200 constructed by 12×4 inductor arrays.

For example, assuming that searching starts from an inductor on (X0, Y0) coordinates, it is determined whether a coordinate value of Y0 in the (X0, Y0) coordinates is less than or equal to 3. When the coordinate value of Y0 is less than or equal to 3, the searching signal is transmitted to a current point. Next, it is checked whether a response signal to the transmitted searching signal is received from the sensor unit 100. When the response signal is not received, the coordinate value of Y0 is increased from a current value by 1. Then, it is checked whether a coordinate value of Y1 is less than or equal to 3 and the foregoing procedures repeat. Using the above-mentioned procedures, when the coordinate value of Y is increased to 3, it is checked whether a coordinate value of a currently searching X0 is less than or equal to 11. When the coordinate value of X0 is less than or equal to 11, after a coordinate value of X is increased from a current value by 1 and the coordinate value of Y returns to 0, the foregoing procedures repeat to perform the searching operation. If a response signal is received from the sensor unit 100, coordinate values of a corresponding point and the received response signal are stored when the response signal is received, and then a searching operation in a next point is achieved. Subsequently, a coordinate value of X is increased to 12, an automatic sensor searching is terminated. When a sensor searching is performed in such a manner, a searching operation can be advanced in a coordinate increase order as shown in FIG. 7. Such a searching method is by way of example only. Various searching methods such as a zigzag method are possible.

The automatic constructing step (S3) recognizes a type and a location of the sensor unit 100 searched using the automatic sensor searching step (S2).

Since the location of the sensor unit 100 is a location corresponding to coordinate values of (X, Y) in which a response signal is received from the sensor unit 100, the coordinate values are recorded so that the location can be recognized. The type of the sensor unit 100 can be recognized by using type information included in the received response signal. At this time, a set sensing cycle and power transmission strength are determined according to the recognized type of the sensor unit 100, and power is supplied to the sensor unit according to the set values. Further, when the number of recognized types of the sensor unit 100 is equal to or greater than 2, power can be simultaneously or alternately supplied to respective sensor units. The sensor unit 100 may receive the power from the control unit 200 and produce a power source to measure a biological signal. In this case, a biological signal measured by the sensor chip 140 may be amplified, filtered, and converted into digital data, or be transmitted in a raw data state.

In the information collecting step (S4), when the biological signal is received from the senor unit 100 in the raw data state using the automatic constructing step (S3), the received biological signal can be amplified, filtered, and converted into digital data, and be stored using compression/encryption.

Although embodiments in accordance with the present invention have been described in detail hereinabove, it should be understood that many variations and modifications of the basic inventive concept herein described, which may appear to those skilled in the art, will still fall within the spirit and scope of the exemplary embodiments of the present invention as defined in the appended claims.

What is claimed is:

1. A wearable monitoring apparatus for continuously monitoring a biological signal, comprising:
    a sensor unit for measuring a biological signal from a human body, wherein the sensor unit is configured to be adhered to a skin;
    a control unit that transmits a searching signal for searching a location of the sensor unit;
    wherein upon receiving the searching signal, the sensor unit transmits a response signal to the control unit, the response signal containing information corresponding to a type of the sensor unit;
    wherein after the sensor unit transmits the response signal, the control unit supplies power to the sensor unit, and the sensor unit measures the biological signal and transmits the biological signal to the control unit; and
    wherein the control unit is formed to be wearable.

2. The wearable monitoring apparatus according to claim 1, wherein the sensor unit comprises:
    an adhesive layer having adhesion and flexibility;
    an inductor that operably connects the sensor unit to the control unit by wireless means using near field coupling;
    a sensing electrode for sensing the biological signal;
    a sensor chip for transmitting the response signal containing the information corresponding to the type of the sensor unit to the control unit in response to receiving the searching signal from the control unit, measuring the biological signal using the sensing electrode, and transmitting the measured biological signal to the control unit; and
    a molding portion formed to cover the sensor chip to prevent the sensor chip from being damaged,
    wherein at least one of the inductor and the sensing electrode is formed by printing a conductive material on a fiber.

3. The wearable monitoring apparatus according to claim 2, wherein the control unit comprises:
    a plurality of inductors that operably connect the control unit to the sensor unit by wireless means using near field coupling, wherein the plurality of inductors are arrayed in a coordinate matrix pattern;
    a power supply for transmitting the searching signal and supplying the power to the sensor unit; and
    a network controller that; (1) transmits the searching signal in a set coordinate order using the plurality of inductors, (2) receives the response signal from the sensor unit, (3) stores the information corresponding to the type of the sensor unit, (4) stores coordinate information of one inductor of the plurality of inductors that received the response signal, (5) supplies the power to the sensor unit in an amount that meets a set sensing cycle and power transmission strength based on the type of the sensor unit using the one inductor having received the response signal, (6) receives the biological signal measured by the sensor unit, and (7) stores the received biological signal;
    wherein the network controller is connected to the plurality of inductors; and
    wherein the plurality of inductors are formed by printing a conductive material on a fiber.

4. The wearable monitoring apparatus according to claim 1, wherein the sensor unit comprises:
    an adhesive layer having adhesion and flexibility;
    a first connector that operably connects the sensor unit to the control unit by wired means, wherein the first connector is capable of being attached and detached to the control unit;
    a sensing electrode for sensing the biological signal;
    a sensor chip for transmitting the response signal containing the information corresponding to the type of the sensor unit to the control unit in response to receiving the searching signal from the control unit, measuring the biological signal using the sensing electrode, and transmitting the measured biological signal to the control unit; and
    a molding portion formed to cover the sensor chip to prevent the sensor chip from being damaged,
    wherein the sensing electrode is formed by printing a conductive material on a fiber.

5. The wearable monitoring apparatus according to claim 4, wherein the control unit comprises:
    a plurality of second connectors that operably connect the control unit to the sensor unit by wired means using the first connector,
    wherein the plurality of second connectors are arrayed in a coordinate matrix pattern and are capable of being attached to and detached from the sensor unit;
    a power supply for providing the searching signal and power to be transmitted to the sensor unit; and
    a network controller that; (1) transmits the searching signal in a set coordinate order using the plurality of second connectors, (2) receives the response signal from the sensor unit, (3) stores the information corresponding to the type of the sensor unit, (4) stores coordinate information of one of the second connectors that received the response signal, (5) transfers the power to the sensor unit in an amount that meets a set sensing cycle and power transmission strength based on the type of the sensor unit using the one of the second connectors having received the response signal, (6) receives the biological signal measured by the sensor unit, and (7) stores the received biological signal;
    wherein the network controller is connected to the plurality of second connectors.

6. The wearable monitoring apparatus according to claim 5, wherein the first connector and the second connectors are configured in a form of a hook and loop fastener, a button, a zipper, or a conductive contact, and are made of a conductive material.

7. The wearable monitoring apparatus according to claim 1, wherein the sensor unit is devoid of a power supply.

8. A method of driving the wearable monitoring apparatus according to claim 1, comprising the steps of:
(i) the control unit automatically transmitting the searching signal to determine the location of the sensor unit;
(ii) the control unit supplying the power to the sensor unit, the sensor unit measuring the biological signal upon receiving the power; and
(iii) the sensor unit transmitting the biological signal to the control unit.

9. The method according to claim 8, wherein step (i) comprises:
transmitting the searching signal in a set coordinate order using a plurality of inductors arrayed on the control unit in a coordinate matrix pattern;
checking whether the response signal containing the information corresponding to the type of the sensor unit as a response to the searching signal is received; and
storing the response signal and coordinate values of one inductor of the plurality of inductors that received the response signal when the response signal is received, and
step (ii) comprises:
recognizing the type of the sensor unit using the response signal;
supplying the power with a set sensing cycle and power transmission strength to the sensor unit using the one inductor having received the response signal according to the type of the sensor unit; and
measuring the biological signal using the sensor unit,
wherein the sensor unit and the control unit transmit and receive data in a wireless connection manner using near field coupling to and from each other.

10. The method according to claim 9, wherein step (i) further comprises transmitting the searching signal using another inductor on next coordinates after storage of the response signal and the coordinate values of the one inductor having received the response signal is terminated, and checking whether the response signal is received.

11. The method according to claim 9, wherein step (ii) further comprises supplying power with different sensing cycles to respective sensor units when there are at least two types of the sensor units.

12. The method according to claim 8, wherein step (i) comprises:
transmitting the searching signal in a set coordinate order using, a plurality of connectors arrayed on the control unit in a coordinate matrix pattern;
checking whether the response signal containing the information corresponding to the type of the sensor unit as a response to the searching signal is received; and
storing the response signal and coordinate values of one connector of the plurality of connectors that received the response signal when the response signal is received, and
step (ii) comprises:
recognizing the type of the sensor unit using the response signal;
supplying the power with a set sensing cycle and power transmission strength to the sensor unit using the one connector having received the response signal according to the type of the sensor unit; and
measuring the biological signal using the sensor unit,
the sensor unit and the control unit transmitting and receiving data in a wired connection manner using the connector to and from each other.

13. The method according to claim 12, wherein step (i) further comprises transmitting the searching signal using another connector on next coordinates after storage of the response signal and the coordinate values of the one connector having received the response signal is terminated, and checking whether the response signal is received.

14. The method according to claim 12, wherein step (ii) further comprises supplying power with different sensing cycles to respective sensor units when there are at least two types of the sensor units.

15. The method according to claim 8, wherein step(iii) comprises:
amplifying, filtering and converting into digital data the biological signal measured by the sensor, and transmitting the digital data to the control unit; and
compressing, encrypting, and storing the digital biological signal transmitted to the control unit.

16. A sensor unit of a wearable monitoring apparatus that is configured to be adhered to a human body for measuring a biological signal, comprising:
an adhesive layer having adhesion and flexibility;
an inductor that operably connects the sensor unit to a control unit by wireless means using near field coupling, the control unit collecting the biological signal measured by the sensor unit;
a sensing electrode that measures the biological signal;
a sensor chip that transmits a response signal containing information corresponding to a type of the sensor unit to the control unit in response to the sensor unit receiving a searching signal from the control unit, receives power from the control unit to measure the biological signal using the sensing electrode, and transmits the measured biological signal to the control unit; and
a molding portion formed to cover the sensor chip to prevent the sensor chip from being damaged,
wherein at least one of the inductor and the sensing electrode is formed by printing a conductive material on a fiber.

17. The sensor unit of claim 16, further comprising the sensor unit being devoid of a power supply.

18. A sensor unit of a wearable monitoring apparatus that is configured to be adhered to a human body for measuring a biological signal, comprising:
an adhesive layer having adhesion and flexibility;
a connector that operably connects the sensor unit to a control unit by wired means, the control unit collecting the biological signal measured by the sensor unit, wherein the connector is able to be attached to and detached from the control unit;
a sensing electrode that measures the biological signal;
a sensor chip that transmits a response signal containing information corresponding to a type of the sensor unit to the control unit in response to the sensor unit receiving a searching signal from the control unit, measures the biological signal using the sensing electrode, and transmits the measured biological signal to the control unit; and
a molding portion formed to cover the sensor chip to prevent the sensor chip from being damaged,
wherein the sensing electrode is formed by printing a conductive material on a fiber.

19. A control unit of a wearable monitoring apparatus for collecting a biological signal measured by a sensor unit configured to be adhered to a human body, comprising:

a plurality of inductors that operably connects the control unit to the sensor unit by wireless means using near field coupling, wherein the plurality of inductors are arrayed in a coordinate matrix pattern;

a power supply that transmits a searching signal to the sensor unit and supplies power to the sensor unit; and a network controller that (1); transmits the searching signal in a set coordinate order using the plurality of inductors, (2) receives a response signal containing information corresponding to a type of the sensor unit as a response to the searching signal, (3) stores the information corresponding to the type of the sensor unit, (4) stores coordinate information of one inductor of the plurality of inductors that received the response signal, (5) supplies the power to the sensor unit in an amount that meets a set sensing cycle and power transmission strength based on the type of the sensor unit using the one inductor that received the response signal, (6) receives the biological signal measured by the sensor unit, and (7) stores the received biological signal, wherein the network controller is connected to the plurality of inductors, wherein the plurality of inductors are formed by printing a conductive material on a fiber.

20. A control unit of a wearable monitoring apparatus for collecting a biological signal measured by a sensor unit configured to be adhered to a human body, comprising:

a plurality of connectors for operably connecting the control unit to the sensor unit by wired means, wherein the plurality of connectors are arrayed in a coordinate matrix pattern and are capable of being attached to and detached from the sensor unit measuring the biological signal;

a power supply that transmits a searching signal to the sensor unit and supplies power to the sensor unit; and a network controller that; (1) transmits the searching signal in a set coordinate order using the plurality of connectors, (2) receives a response signal containing information corresponding to a type of the sensor unit as a response to the searching signal, (3) stores the information corresponding to the type of the sensor unit, (4) stores coordinate information of one connector of the plurality of connectors that received the response signal, (5) supplies power to the sensor unit in an amount that meets a set sensing cycle and power transmission strength based on the type of the sensor unit through the one connector having received the response signal, (6) receives the biological signal measured by the sensor unit, and (7) stores the received biological signal, wherein the network controller is connected to the plurality of connectors.

* * * * *